United States Patent [19]
Abel

[11] Patent Number: 5,163,914
[45] Date of Patent: Nov. 17, 1992

[54] SUPPORT FOR A RESPIRATOR HOSE

[76] Inventor: Elaine R. Abel, P.O. Box 91538, Henderson, Nev. 89009

[21] Appl. No.: 781,876

[22] Filed: Oct. 24, 1991

[51] Int. Cl.⁵ ........................................... A61M 25/02
[52] U.S. Cl. ........................ 604/180; 128/DIG. 15; 128/DIG. 26; 128/200.24
[58] Field of Search .......... 128/204.18, 912, DIG. 15, 128/DIG. 26, 200.24; 604/174, 177, 178, 179, 180; 206/364, 365, 366, 438; 24/442, 306; 2/DIG. 6

[56] References Cited

U.S. PATENT DOCUMENTS

| | | | |
|---|---|---|---|
| 2,669,231 | 2/1954 | Fisher | 604/179 |
| 3,430,300 | 3/1969 | Doan | 604/180 X |
| 3,696,920 | 10/1972 | Lahay | 128/DIG. 26 X |
| 3,834,380 | 9/1974 | Boyd | 604/180 |
| 3,918,446 | 11/1975 | Buttaravoli | 604/180 |
| 4,129,128 | 12/1978 | McFarlane | 128/DIG. 26 X |
| 4,333,468 | 6/1982 | Geist | 128/DIG. 26 X |
| 4,336,806 | 6/1982 | Eldridge, Jr. | 128/DIG. 26 X |
| 4,416,664 | 11/1983 | Womack | 604/174 |
| 4,574,798 | 3/1986 | Heitzman | 128/DIG. 26 X |
| 4,617,017 | 10/1986 | Hubbard et al. | 128/DIG. 26 X |
| 4,639,980 | 2/1987 | Peterson | 128/DIG. 26 X |
| 4,726,716 | 2/1988 | McGuire | 604/180 |
| 4,743,232 | 5/1988 | Kruger | 604/180 |
| 4,838,878 | 6/1989 | Kalt et al. | 128/DIG. 26 X |
| 4,919,654 | 4/1990 | Kalt | 604/180 |
| 4,979,613 | 12/1990 | McLaughlin et al. | 24/442 X |
| 4,988,338 | 1/1991 | Taylor et al. | 604/180 |
| 5,031,282 | 7/1991 | Denaro | 24/306 X |
| 5,082,111 | 1/1992 | Corbitt et al. | 128/DIG. 15 X |

Primary Examiner—Vincent Millin
Assistant Examiner—Sebastiano Passaniti

[57] ABSTRACT

A respirator hose support pad for tracheostomy patients, and method of use thereof for providing strain relief, and for reducing respirator machine induced intermittent hose movement, vibration, and fluid passage from the respirator hose into the patient. The support pad has a hook and loop fastener structure on the central bottom surface for releasable attachment to a patient's garment in the upper central chest area. The terminal oppositely disposed ends of the pad each have an extending flange which serve as handles. The pad additionally has a detachable flexible belt on the top surface for adjustable loose securement of the respirator hose onto the top of the pad. When the belt is properly affixed over a respirator hose, the hose is loosely retained between the pad and belt, and may slide back and forth across the pad to prevent excessive pulling on the tracheostomy tube as the patient moves. The interior of the pad contains a compressible and somewhat resilient padding material to dampen the irritating and painful effect on the patient's tracheostomy of the respirator hose vibrations and jerking movements caused by the intermittent positive pressure introduction of gasses into the patient. The somewhat thickened pad is additionally utilized to help maintain the respirator hose angling downhill in order to direct fluids which naturally condense in the respirator hose away from the patient's tracheostomy tube and lungs.

5 Claims, 4 Drawing Sheets

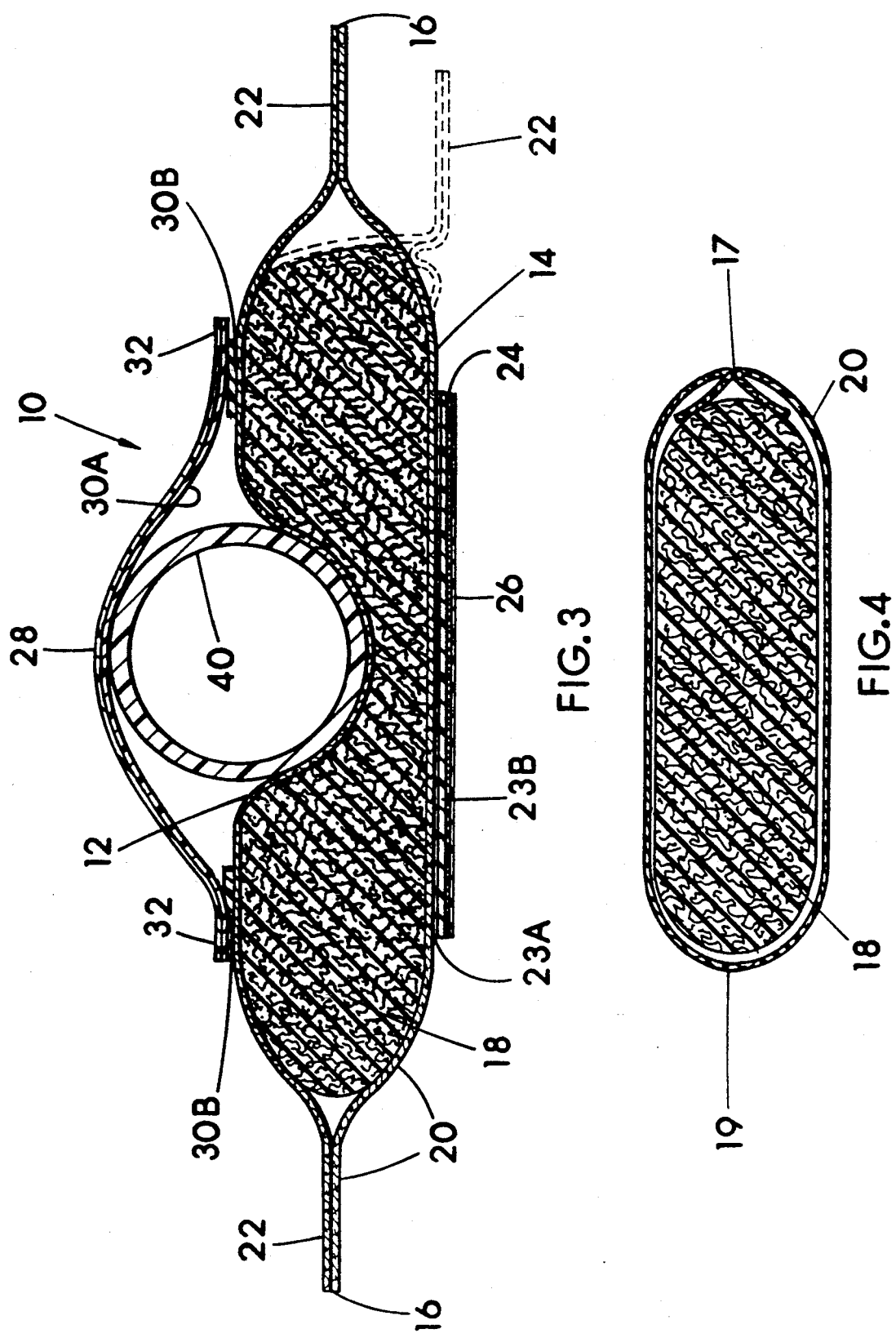

SUPPORT FOR A RESPIRATOR HOSE

BACKGROUND OF THE INVENTION

1. Field of the Invention

This invention includes a support pad for a human tracheostomy patient's ventilator or respirator hose, and a method or procedure of using the support pad. The support pad attaches to the tracheostomy patient's garment in the chest area, and is structured to maintain the respirator hose in a generally straight-line approach to the tracheostomy tube to assist in relieving pulling pressures applied to the tracheostomy tube by the respirator hose. Additionally the support pad is structured to dampen the vibration and intermittent jerking movements transferred into the tracheostomy tube by the respirator hose. The invention also addresses the problem of fluid in the respirator hose flowing into the tracheostomy tube and the patient's lungs.

2. Description of the Past Art

People who are experiencing various types of respiratory distress are often fitted with an artificial airway to assist in breathing. This procedure generally involves the creation of an opening or stoma in the throat or trachea of the patient. The stoma is then fitted with a tracheostomy tube assembly which is releasably affixed to the patient with a tether extending around the patient's neck. With extreme respiratory distress, the tracheostomy tube is attached to an electro-mechanical respirator machine, via a somewhat flexible respirator hose, which forces air into the patient's lungs. The most commonly used respirator machines, often called ventilators, introduce gasses such as oxygen enriched air on an intermittent positive pressure basis to force the air into the lungs at intervals between periods of neutral pressure or vacuum. The intermittent positive pressure introduction of air into the respirator hose causes the hose to move back and forth slightly in a jerking fashion as the hose stiffens and then relaxes with the increased and then decreased pressures within the hose. The back and forth jerking movements in the respirator hose are transferred into the tracheostomy tube and can be felt by the patient. The natural operation of the most common respirator or ventilator machines, which include an electrical motor, also creates a slight constant vibration, mostly from the motor, which is often transferred through the respirator hose to the tracheostomy tube to be felt by the patient. Although this intermittent jerking movement and vibration may at first appear to be generally insignificant, over an extended period of time these slight but constant movements can cause irritation and pain in the stoma surrounding the tracheostomy tube. This situation is particularly applicable to long term patients, where a sensitive stoma causes routine cleaning and changing of the tracheostomy tube to be a painful ordeal, and an irritated and debilitated stoma is more prone to infection. An infected stoma can lead to serious lung infections and death.

An even further problem associated with the care of the tracheostomy patients connected to respirators via hoses are the pulling stresses applied directly to the tracheostomy tube by the respirator hose. The pulling stresses applied to the tracheostomy tube occur most often as a patient moves around in bed, turning from one side to the other. These pulling stresses applied to the tracheostomy tube can be felt by the patient, and may be painful, often contributing to an irritated and debilitated stoma.

Another problem associated with the care of the tracheostomy patient on a respirator is inadvertent introduction of moisture condensation from the respirator hose into the patient's trachea and lungs. The most common of respirators are designed to add moisture to the gasses in the form of a very fine fluid mist or vapor, which prevents the lining of the trachea from becoming dehydrated. Some of this moisture unfortunately collects on the interior of the respirator hose and may eventually pools in low points or bends. If the respirator hose is elevated above the level of the tracheostomy tube, the fluid condensation can flow down into the tube and into the patient's lungs. This often occurs at night when the patient turns from one position to another, where fluid collected in one bend of the hose is displaced into the tracheostomy tube when the patient changes position. A procedure commonly used to reduce this problem is to routinely manually drain the hose by manipulating the bends containing the fluid down toward the end of the hose attached to the respirator where the fluid is deposited into a fluid collecting vial. Unfortunately this manual hose draining procedure is not always carried out consistently, and it is most often not performed during the night since the patient would be disturbed.

Several prior art devices have been developed which are designed to support and secure tubing or hoses of various types. One such device is shown by Eldridge, Jr., in U.S. Pat. No. 4,336,806. Eldridge, Jr. shows a self-adhesive backing strip designed to be folded over and releasably secured onto itself with magnets, also securing a section of tubing in the fold. Eldgridge's device is primarily designed for supporting small diameter tubing such as a nasogastric line, cautery cords or intravenous tubing, and allows for little or no movement of the hose through the hose support.

Another hose clamping structure is taught by Kalt et al, in U.S. Pat. No. 4,838,878. Kalt's device includes a base for adhering to an object, and a flap for securing the tubing to the base. Kalt uses hook and loop fastening means to releasibly secure the flap in a closed position over a hose. Kalt does not adequately address the problems of fluid draining into a tracheostomy tube, or of harmful vibration and intermittent jerking effects created in a tracheostomy tube by the normal intermittent introduction of gasses by a ventilator or respirator.

A third hose clamping structure is taught by Heitzman in his U.S. Pat. No. 4,574,798. Heitzman's surgical appliance support includes a support member designed to be fitted to the patient's chest or back with the use of detachable straps. The Heitzman device appears to be quite complicated and expensive to manufacture, and possibly difficult to apply and remove particularly by the user.

The related past art does not adequately, both structurally and instructionally, address by way of stating proper procedure in combination with a proper structure, the problems of fluid draining into a tracheostomy tube, or of harmful vibration and intermittent jerking effects created in a tracheostomy tube by the normal intermittent introduction of gasses by a respirator, and the pulling stresses applied to the tracheostomy tube by the weight and pull of the respirator hose, particularly when the patient moves about. Therefore there is a significant need for a properly structured support pad for a respirator hose, and a proper method, system or procedure of use thereof for tracheostomy patients.

SUMMARY OF THE INVENTION

The invention of this disclosure includes a support pad for a respirator or ventilator hose, and method or procedure of use thereof with tracheostomy patients connected to respirator or ventilator machines via a respirator hose. The support pad and the proper use thereof is simple enough so that many patients may utilize the invention themselves without the necessity of assistance from others, such as a nurse. One preferred embodiment of the support pad is structured with the intent to be able to be manufactured inexpensively enough to be sold at a sufficiently low price to allow the pad to be effectively disposable, and inexpensive enough to hopefully encourage frequent replacement and thereby possibly reduce the risk of infection to the patient from a soiled support pad. Additionally, a disposable support pad will add convenience to using the pad by eliminating the need to wash and dry it periodically. The support pad could be structured to be reuseable instead of disposable and still remain within the scope of the invention.

The pillow-like support pad is comprised of a soft somewhat resilient interior batting with a flexible material outer covering. The preferred shape of the support pad is roughly rectangular. The top of the pad has a centrally affixed flexible belt for lightly securing the respirator hose centered in position on top of the pad. The belt is detachably affixed to the pad on at least one and preferably both proximal ends thereof by hook and loop fasteners for increased convenience and effectiveness during use. Affixed centrally to the bottom surface of the pad, oppositely disposed from the detachable belt, is a hook and loop type structural arrangement for releasably affixing the pad to the patient's garment in the upper central chest area. The flexible outer covering of the pad extends slightly beyond the ends of the interior batting, creating two oppositely disposed relatively thin flexible flanges. These flanges may be used as areas through which to safety pin the pad to the patient's garment if desired instead of, or in combination with the central bottom hook and loop fastener arrangement. These extending flanges additionally serve as handles for grasping and pulling on the pad during removal of the pad from the patient's garment.

In use, the pad is attached lengthwise oriented across the patient's garment in the upper central chest area close to the tracheostomy tube using the bottom hook and loop fastener, and additionally using safety pins through the flanges if desired for fail-safe securement of the pad to the garment. One end of the belt on the top of the pad is lifted and the respirator hose is positioned over the pad, and the free end of the belt is then reattached to trap the hose between the pad and the belt. At this point, the support pad is positioned between the patient's chest and the respirator hose, and in use, due to the soft resilient nature of the pad, most vibration and pressure change induced movement in the respirator hose will be absorbed or dampened in the short portion of the hose extending between the pad and the tracheostomy tube. When properly affixed, the belt of the pad is loose enough to allow sliding movement of the hose between the smooth or slick surfaces of the top of the pad and the underside of the belt resting lightly on the top of the respirator hose. The belt is affixed loosely over the hose, being not so secure that it causes tension to be applied directly to the tracheostomy tube if the patient moves her neck and head, a common action by a patient which effectively changes the distance between the support pad and the tracheostomy tube. Therefore, if the patient should tilt her head back which effectively increases the distance between the tracheostomy tube and the support pad, the respirator hose may be easily pulled through the loose belt, and excessive tension on the tracheostomy tube is thus avoided. The respirator hose, due to a certain degree of stiffness therein, will also slide back through the belt, sliding over the support pad if the patient repositions her neck closer to the support pad. Normally, this sliding of the hose over the pad as the patient repositions her neck is only about one to ten centimeters in distance. The loose belt does however restrict lateral movement of the respirator hose, maintaining the respirator hose in a generally straight-line approach to the patient's tracheostomy tube, coming straight up from the center of the patient's chest and attaching to the patient's tracheostomy tube which is placed in the center front of the patient's neck. This straight-line loose or slidable approach of the hose to the patient's tracheostomy tube assists in preventing the hose from falling to one side of the pad, and thus in helping to avoid tension on the tracheostomy tube from both straight-line pulls and sideways angled pulls.

With the pad properly placed on the patient's garment in the central upper chest area, the short section of respirator hose positioned between the tracheostomy tube and the pad is maintained generally straight, while a downward angle is naturally formed in the much longer portion of the respirator hose on the other side of the pad, between the hose support pad and the respirator machine. Water condensation which normally occurs in the respirator hose will therefore drain down into a collection vial typically located on a lower section of the respirator hose adjacent the respirator machine. The support pad elevates the end of the respirator hose attached to the tracheostomy tube to a degree, and this slight elevating in combination with the maintained straight-line approach of the hose to the tracheostomy tube has been found to greatly assist in preventing fluid condensation from entering the tracheostomy tube and the patient's lungs. The short section of the hose between the properly placed hose support pad and the tracheostomy tube is too short, about twenty or less centimeters normally, to collect an appreciable amount of condensation. If the patient's garment is generally secure, the patient can turn from side to side while in bed with the support pad helping to dampen direct pull on the tracheostomy tube during movement. The longer portion of the respirator hose will generally be positioned downward even when the patient turns on her side, due to the pliability of the typical respirator hose and the pull of gravity on a relatively long length of the hose. Thus the properly placed hose support pad helps to prevent water condensation from back flowing into the tracheostomy tube even when the patient is positioned on her side.

The purpose of the support pad is not to prevent all movement of the respirator hose, but is primarily to serve as a hose strain relief; to dampen vibrations and brief jerking movements in the hose; and to help prevent introduction of fluid into the patient's lungs.

Therefore, a primary object of my invention is to provide a properly structured support pad for a respirator hose of a tracheostomy patient, and a method, system, or procedure of use thereof which provides strain relief, reduces the minor movements and operational vibrations transferred to a tracheostomy tube from a respirator hose, while at the same time allowing the patient a degree of freedom to move about.

A further object of my invention is to provide the above in a support pad for a respirator hose which when properly used will assist in preventing fluid in the hose from entering the tracheostomy tube and the patient's lungs.

A still further object is to provide the above in a support pad for a respirator hose which is structured to be simple enough to be properly utilized by many patients without the assistance of others.

A further object of my invention is to provide the above in a support pad for a respirator hose which is structured with the intent to be able to be manufactured sufficiently inexpensively and therefor sold at a low enough price relative to the cost of washing and drying to be effectively disposable in order to provide for improved infection control, convenience of use, and cost effectiveness.

These and other objects and advantages of my invention should become apparent from reading the remaining description along with examination of the accompanying drawings.

BRIEF DESCRIPTION OF THE DRAWINGS

FIG. 3 is a lengthwise cross sectional view of my hose support pad of FIG. 1 illustrating the relative placement of a respirator hose on the top of the pad with the hose restrained against lateral movement by the top belt placed loosely across the top of the respirator hose. Also shown in dotted lines is one of the two flanges to illustrate the flanges being capable of being brought down to lie in about the same plane as the bottom of the pad;

FIG. 4 is a widthwise cross sectional view of my hose support pad taken at line 4 of FIG. 2, showing a side fold and a side seam of the one piece outer covering of the pad;

BEST MODE FOR CARRYING OUT THE INVENTION

Figure 1:
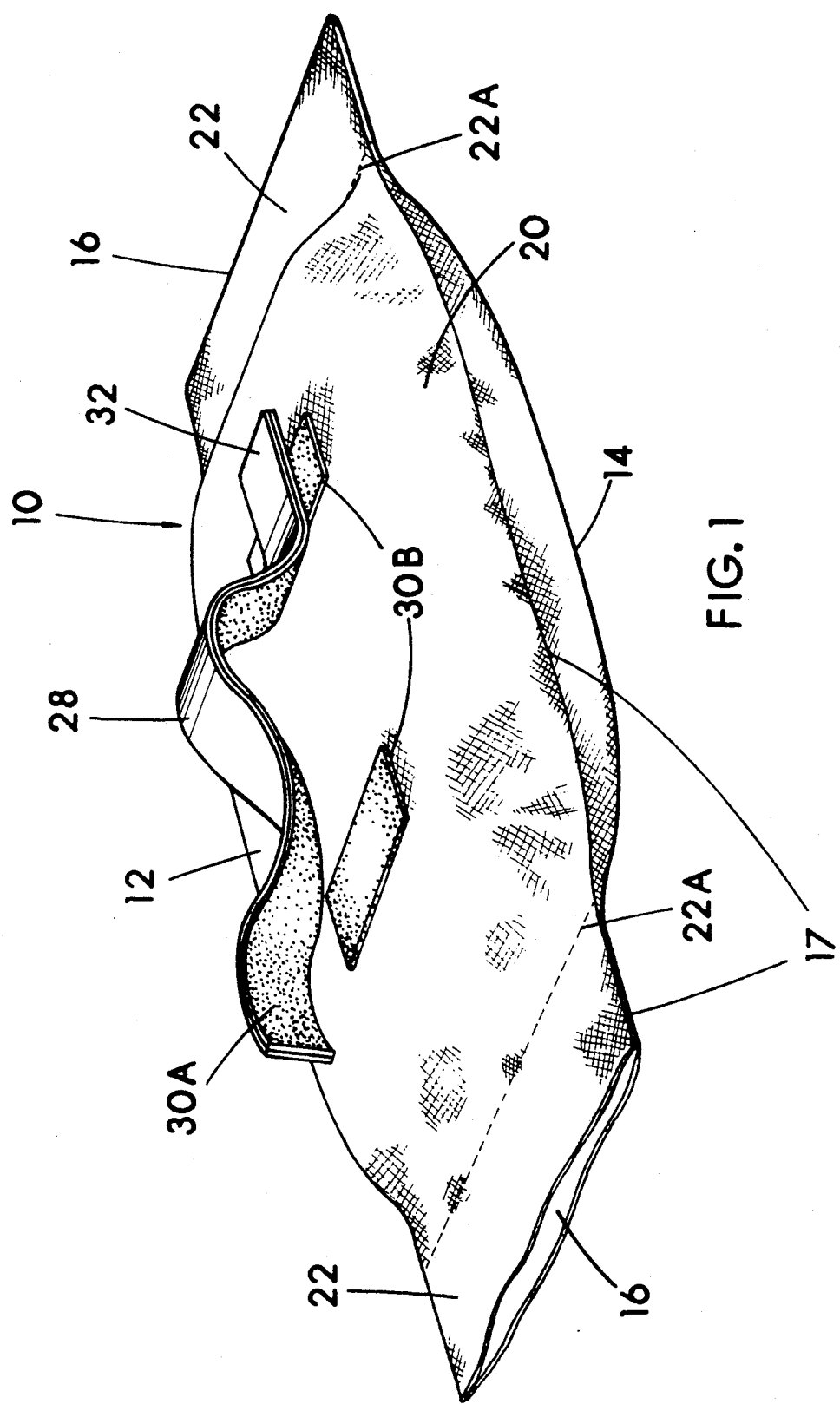
FIG. 1 is a perspective top view of a preferred embodiment of my support pad for a respirator hose showing the detachable belt affixed at one end and detached at the other end for illustrative purposes.

Referring now to the drawing figures in general and to a preferred embodiment of my support pad 10 shown therein. Pad 10 is an elongated rectangular pillow-like structure which may be feasibly sized around fifteen to twenty-five centimeters in length from end 16 to the oppositely disposed end 16; six to fifteen centimeters in width between side seam 17 and side fold 19; and three to eight centimeters in height or thickness from top surface 12 to bottom surface 14. The shape and size of pad 10 could possibly be varied somewhat from the above dimensional ranges and still remain feasible. Pad 10 includes the broad top surface 12, the oppositely disposed broad bottom surface 14, two narrow lengthwise oppositely disposed side edges defined by side fold 19 and side seam 17, and the two terminal ends 16 oppositely disposed from one another at the ends of flanges 22 which are oppositely disposed from one another at the two ends of pad 10.

An outer covering 20 of pad 10 which envelopes batting 18 may be made of a single piece of rectangular flat flexible material which is folded wherein one of the two lengthwise sides of pad 10 is a sewn or otherwise affixed side seam 17 while the other side is not sewn but merely formed by the fold 19 in the outer covering 20 of pad 10, and will be further explained later. Pad 10 is additionally comprised of the soft or compressible somewhat resilient interior batting 18 material inserted between the two layers formed by folding the flexible outer covering 20. Batting 18 may be cotton or a cotton-like similarly somewhat resilient and compressible fiber. Batting 18 might possibly be a low density foamed plastic or rubber product. Batting 18 needs to be quite soft, generally soft enough to allow the weight of a section of respirator hose 40 to compress pad 10 to a small degree and thereby create greater surface area contact between hose 40 and pad 10 which will provide enhanced shock absorbtion, see FIG. 3. During use in order to achieve this greater surface area contact and thus shock absorbtion, the respirator hose 40 may be pressed downward by hand into pad 10 if desired. The softness and slight resiliency of the batting 18 when used with a highly flexible outer covering 20 gives pad 10 the characteristics of being quite soft and slightly resilient, at least in the area of batting 18. Cotton batting or a synthetic equivalent has been found to be quite mechanically feasible and cost effective for the interior batting 18 of pad 10. The thickness of the batting 18 is also somewhat important in that it must be adequately thick to effectively absorb shock vibrations.

Figure 2:
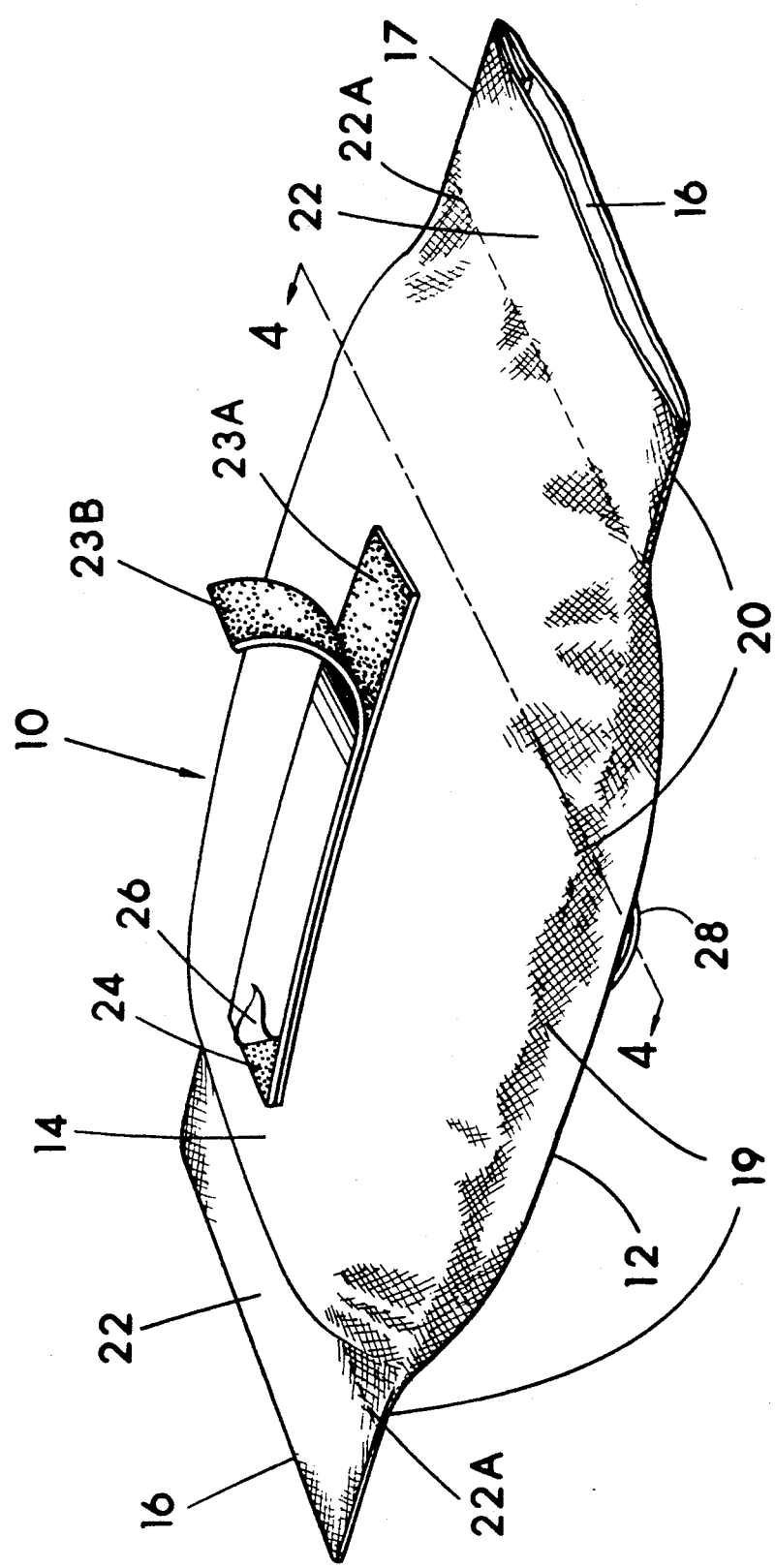
FIG. 2 is a bottom perspective view of my hose support pad of FIG. 1 showing the hook and loop fastener structure which includes a peel-and-stick adhesive backing for attaching one portion of the hook and loop to a patient's garment.
Figure 5:
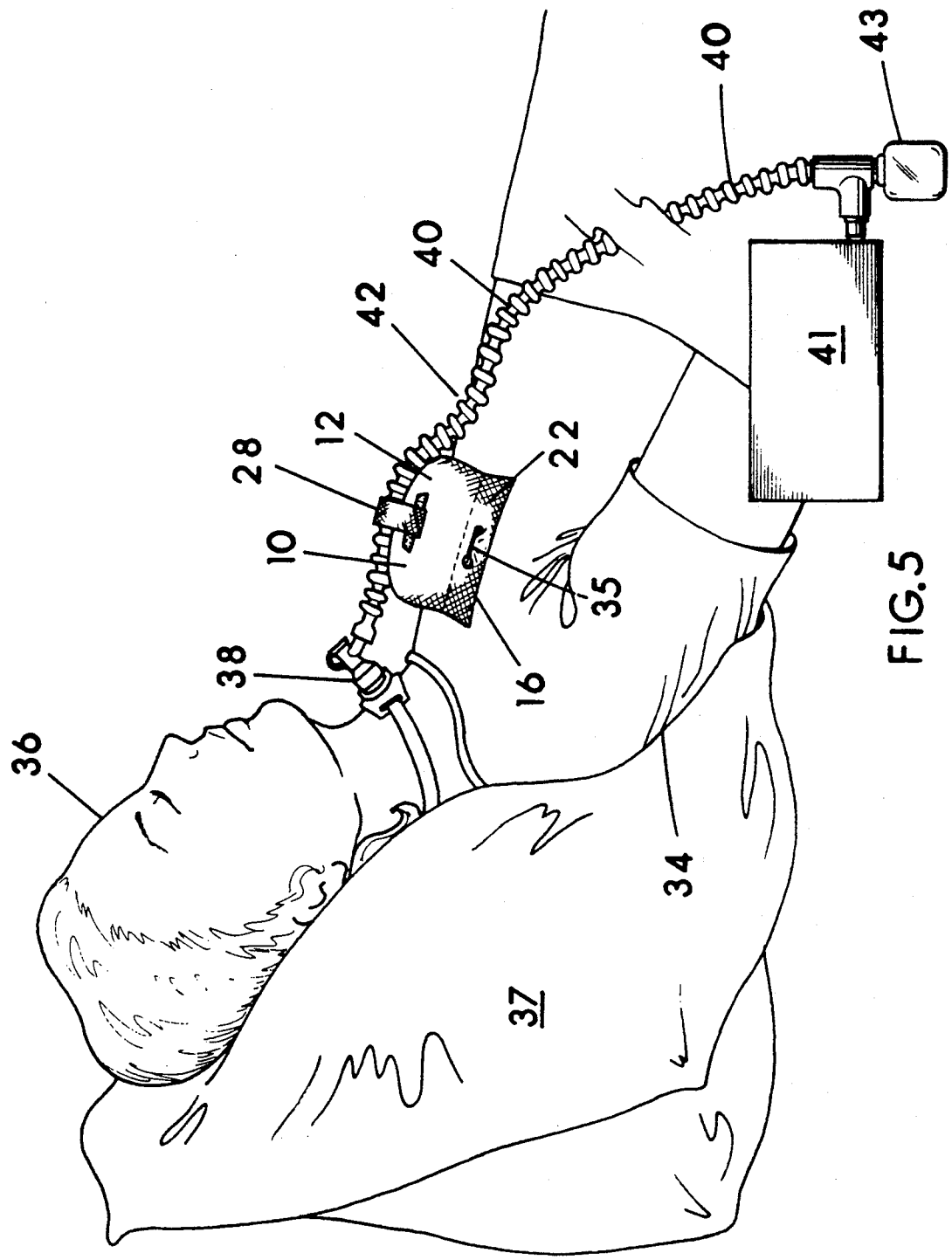
FIG. 5 is an in-use illustration depicting a proper relative placement of my hose support pad of FIG. 1 and a respirator hose during use on a tracheostomy patient while lying in bed.

Batting 18 is completely enveloped by the flexible outer covering 20. As stated previously, covering 20 appears to be most economically made of a single rectangular panel of thin and flat flexible material wherein one of the two lengthwise sides of pad 10 extending from one end 16 to the oppositely disposed end 16 is merely formed by folding the panel in-two at fold 19, while the other side is a sewn or otherwise affixed side seam 17 of the two over-lapped lengthwise edges of the panel brought together by the folding at 19. See FIG. 3 and 4. Side seam 17 also extends from one end 16 to the oppositely disposed end 16 of pad 10. As may be ascertained from FIG. 4, I prefer folding outer covering 20 and then sewing side seam 17, followed by inverting what is in effect a tube so as to face the seam allowance of the sewn side seam 17 inward, with this being to avoid having to trim the material and to provide a neater overall appearance to pad 10. Outer covering 20 may be comprised of moisture pervious or moisture impervious woven fabric or plastic sheeting, or a durable paper material which is relatively smooth and slick at least on the side which will be the exterior or exposed top surface 12 underneath hose 40. A smooth and slick top surface 12 on which respirator hose 40 rests on pad 10 will reduce frictional adhesion between covering 20 and the hose 40, and thus allow the hose 40 to easily slide over the pad 10. One of the more suitable materials from which to make covering 20 considering purchase cost and desired function is a non-woven medical grade disposal paper or wood pulp-based material, some varieties of which contain synthetic fibers for added tear strength Such material is commonly used for many disposable items in hospitals. This type of paper or wood pulp-based material for covering 20 is available from several U.S. manufacturers including the Kimberly-Clark Corp. of 1400 Holcomb Bridge Rd., Roswell, Ga. U.S.A.. Outer covering 20 extends about two to five centimeters beyond the ends of interior batting 18 to form two oppositely disposed thin and flat flexible flanges 22, as shown in FIG. 1 and 2. The interior edge of both flanges 22 adjacent batting 18 are seamed with a row of stitching 22A extending transversely from fold 19 to side seam 17. The exterior or terminal ends 16 at flanges 22, which consists of one layer of covering 20 laying on the other layer of the folded covering 20 may be feasibly left un-stitched across the width to assist in keeping the manufacturing cost low without any adverse effects, as may be ascertained from FIG. 1. Seams or stitchings 22A in combination with fold 19 and side seam 17 forms the enclosed area which maintains batting 18 in position in the center of covering 20 and the center of pad 10. Heat, sonic, or adhesive formed seams may be utilized instead of sewn stitches at side seam 17 and stitches 22A to properly fashion outer covering 20 dependant upon the material selected to be used as covering 20, however, sewn stitches for seaming are inexpensive and function well with the paper-based preferred material of outer covering 20. It is not necessary for flanges 22 to contain stuffing or batting material. As one may ascertain from FIG. 3, flanges 22 are long enough and flexible enough to be able to be brought down to lie at least in part in the same plane as bottom surface 14 of pad 10, with this rendering it much easier to fasten the flanges 22 and thus pad 10 with safety pins 35 to a patient's garment 34 as shown in FIG. 5, and also rending the flanges 22 sufficiently long to serve as handles for grasping with the human hand.

Affixed centrally to bottom surface 14 of pad 10 is a hook and loop attachment structure for releasibly attaching pad 10 to a patient's garment 34. This hook and loop attachment structure is comprised of two elongated strips of the mating sections of hook and loop fasteners, and is considered at this time as the primary fastener for attaching pad 10 to a garment 34, with the safety pins 35 passed through flanges 22 being considered a secondary or optional back-up attachment method used in conjunction with the central hook and loop fastener structure. The one mating section of the hook and loop fastener is permanently affixed to the central bottom surface 14 and is designated hook and loop fastener section 23A, with the mating section of the fastener referred to as hook and loop fastener section 23B. The elongated section 23A is placed in lengthwise alignment with the length of pad 10. The backing material of hook and loop fastener section 23A is permanently affixed to bottom surface 14 of pad 10 with the hook or loop portion of this section facing outward or away from pad 10. The attachment of hook and loop fastener section 23A to pad 10 is preferably with sewing although adhesives might be feasible, I prefer sewing the backing material of fastener section 23A to pad 10. The backing material of hook and loop fastener section 23B is covered with a medium or high tack pressure sensitive adhesive 24. Hook and loop fastener section 23B with a pre-coat adhesive 24 is available from Velcro USA Inc., 406 Brown Ave, Manchester, N.H. Adhesive 24 has a peel-off protective covering 26 which protects adhesive 24 from becoming dirty or losing tackiness prior to use. Once removed, protective covering 26 is discarded, and the adhesive 24 may be pressed against the patient's garment 34 to removably affix hook and loop fastener section 23B to garment 34 with the hook or loop portion of the fastener section facing away from the garment 34 to allow mating with the opposite portion of the fastener section 23A attached to the bottom 14 of pad 10. The procedure of pressing adhesive 24 to garment 34 may be performed with both hook and loop sections 23A and 23B affixed to one another and to pad 10 in which case pad 10 would be pressed against the garment 34 to apply pressure to make sure adhesive 24 adhered well to garment 34. As an alternative procedure, hook and loop fastener section 23B may be removed from fastener section 23A and pad 10, followed by removing protective covering 26 and adhering fastener section 23B to garment 34, followed by affixing the hook and loop fastener sections 23A and 23B together which would affix pad 10 releasibly to garment 34. Adhesive 24 should be strong enough so as to remain in place attached to garment 34 should pad 10 be pulled outward wherein the connection between the mated hook and loop fastener sections 23A and 23B should give way and separate first rather than adhesive 24 releasing from garment 34. With the hook and loop fastener sections 23A and 23B coming apart first upon pulling on pad 10, this allows removal and reattachment of pad 10 repeatedly to and from garment 34 without having to remove hook and loop fastener section 23B which is attached to garment 34 by adhesive 24, an advantage since each time adhesive 24 is removed and then reapplied to a garment, the adhesive 24 would have less holding strength. Pulling on a pad 10 attached to a garment 34 when wishing to remove the pad 10 from the garment 34 with hook and loop fastener section 23B left adhered to the garment, may best be accomplished by grasping one flange 22 and pulling the grasped flange 22 toward the opposite flange 22 in order to somewhat roll the pad 10 upward and away from the garment to brake free small portions of the mated sections of the hook and loop fasteners 23 A and 23 B at a time.

Although not shown in the drawings, and not my most preferred method or structure, but possibly feasible, hook and loop fastener sections 23A and 23B could be eliminated and simply replaced with double-sided pressure sensitive adhesive tape which included a peel-and-stick covered adhesive on the exposed side for attaching the pad 10 to a garment 34. The opposite adhesive backed side of the double-sided pressure sensitive tape would be used to attach the pad 10 to the tape. Under this arrangement, it would be more desireable to use double-sided pressure sensitive tape having a relatively stronger adhesive on the side thereof which contacted pad 10, and relatively weaker adhesive on the side of the tape which contacted garment 34, with this being primarily to build in predictability as to which portion was going to separate first when pulling pressure is applied to pad 10 away from garment 34.

Top surface 12 of pad 10 is affixed with an elongated detachable belt 28 affixed centrally and in lengthwise alignment with the length of pad 10. Belt 28 is a narrow flexible strap of fabric or similarly flexible material desirably having one entire surface affixed with hook and loop fastener 30A, and preferably being the softer looped portion of the fastener since the loop portion of hook and loop fastener is relatively smooth and slick when compared to the hook portion, and a smooth and slick surface on belt 28 which rests against respirator hose 40 will reduce frictional adhesion between the belt 28 and the hose 40 and thus allow the hose 40 to easily slide over the pad 10. Belt 28 works well when made flat and about three centimeters wide, and twelve to eighteen centimeters or so long, but must be made sufficiently long to allow attaching the belt 28 very loosely over the top of at least one respirator hose 40 as may be ascertained from FIG. 3. Belt 28 is releasably affixed or affixable at each proximal end of the belt to pad 10 by two small sections of hook and loop fasteners 30B, which are in this case two short rectangular hook portion strips affixed by sewing or another suitable method onto outer covering 20 at top surface 12 adjacent each flange 22, best shown in FIG. 1. Preferably, belt 28 is sufficiently long to allow affixing of the belt 28 over a respirator hose 40, with respirator hose 40 loosely trapped between pad 10 and loop fastener 30A of belt 28 so that the terminal ends of the belt 28 extend outward beyond hook and loop fastener sections 30B to provide unattached extending portions of the belt 28 which serve as handles designated tabs 32 as may be ascertained from FIG. 3. Tabs 32 serve as a finger gripping surface for easier removal of either end of belt 28 from pad 10 to release respirator hose 40. Belt 28 is detachable from pad 10 from either end so that the patient may slide the respirator hose 40 off of pad 10 from either side of pad 10 when getting out of bed, thereby enhancing the patient's options and control over maintaining the respirator hose 40 angling downward, and of which side of the bed from which to leave. My most preferred belt 28 is simply a strip of loop fastener wherein the inherent fastener backing and the loop material is essentially the entire belt 28, eliminating any need for an additional backing or of sewing little patches of loop fastener to a backing material. Such strip form of loop fastener for belt 28 may be inexpensively purchased from many suppliers. Additionally, with this most preferred belt 28 structure, the loop portion 30A of the fastener covers one entire side of belt 28, which allows for very easy alignment and attachment of belt 28 to the small hook fastener squares 30B attached to the covering 20 on top 12 of pad 10. I have considered using snap fasteners and even double-sided pressure sensitive adhesive tape for attaching belt 28 to outer covering 20 of pad 10 instead of the hook and loop arrangement previously described, but believe the hook and loop fastening arrangement to be the most feasible.

In further explanation of the preferred method of use of pad 10, the proper use thereof includes attachment of pad 10 onto the garment 34 of patient 36 in the upper central chest area as shown in FIG. 5 with hook and loop fastener 23A and 23B. Pad 10 should be positioned transversely across the chest of patient 36 with each end 16 facing the sides of patient 36. Pad 10 should be positioned close to tracheostomy tube 38 in a position so that hose 40 may be affixed on top of pad 10 and approach tracheostomy tube 38 in a straight line so that there is little or no bend in respirator hose 40 between tracheostomy tube 38 and pad 10. Although respirator hoses are flexible to a degree, they do exhibit a degree of stiffness which allows them to span short distances with little or no sagging as illustrated in FIG. 5 where hose 40 is spanning the distance between pad 10 and tracheostomy tube 38. The distance between pad 10 and tracheostomy tube 38 can vary considerably, depending on several factors including the stiffness of the hose 40 and the size of the chest of patient 36. My testing has found the distance range of approximately three to twenty centimeters between pad 10 and tracheostomy tube 38 to be acceptable in most cases. If the chest of patient 36 were extended or elevated, such as with a large breasted woman or an exceptionally over weight patient 36, pad 10 would merely be moved closer to tracheostomy tube 38. Even if pad 10 were still slightly elevated above tracheostomy tube 38, the short length of respirator hose 40 positioned between tracheostomy tube 38 and pad 10 should not normally collect sufficient water condensation to cause an appreciable problem.

Respirator hose 40 will sometimes already be attached to tracheostomy tube 38 on one end and to a respirator machine 41 on the other during attachment of pad 10 to garment 34, requiring belt 28 to be detached from pad 10 at least on one end. With one end of belt 28 detached from hook and loop fasteners 30B and folded over to the side, respirator hose 40 is laid transversely across the top central area of pad 10 between the two sections of hook and loop fasteners 30B. The free end of belt 28 is then reattached to the respective hook and loop fastener 30B, placing belt 28 loosely over respirator hose 40. Belt 28 is not secured so tightly as to restrict movement of respirator hose 40 back and forth over pad 28, but merely prevents hose 40 from falling to one side or the other. In FIG. 3, belt 28 is touching hose 40 only due to gravity on belt 28. The weight of hose 40 and the compressibility of interior batting 18 allows hose 40 to sink into pad 10 sufficiently to provide a substantial dampening effect against jerking movement and vibration caused by the operation of the respirator.

When in use, pad 10 is positioned relatively close to tracheostomy tube 38 so there is little to no slack formed in respirator hose 40 which could cause a low point where water condensation could collect, due primarily to the stiffness of a typical respirator hose. However, on the opposite side of pad 10, the longer portion of respirator hose 40 shown at 42 angles downwardly toward respirator machine 41. Water condensation often forms in bent or bowed sections of respirator hose 40, and without the use of pad 10, this pooled fluid is more likely to flow back into tracheostomy tube 38 with certain movements of patient 36 or respirator hose 40. Since pad 10 elevates the end of respirator hose 40 and assists in creating the downward angle in hose 40 in section 42 between pad 10 and fluid collection vial 43, the water condensation is generally prevented from flowing over pad 10 and into tracheostomy tube 38 and the patient's lungs. Patient 36 in FIG. 5 is shown laying on her back with her head and neck elevated by a pillow 37, and although this is an ideal position for the patient as far as fluid flow control, many patients desire to sleep on their sides for at least some of the time. Even when patient 36 turns on one side, downward angled section 42 of hose 40 generally falls downward due to gravity, maintaining the pooled water condensation below the elevated section of respirator hose 40 attached to pad 10. Although the amount of water condensation is relatively small, it would still be quite painful and difficult for patient 36 to expel if it reached the lungs.

When removing respirator hose 40 from pad 10, hose 40 is moved to the side of patient 36 by disconnecting one or the other side of belt 28 from pad 10, being careful not to raise any portion of hose 40 above the opening of tracheostomy tube 38 if possible. Any remaining water condensation collected along respirator hose 40 may and should be drained downward by manually manipulating hose 40, and disposed in collecting vial 43, which is standard equipment on most respirator machines 41. To pull pad 10 away from a garment 34, flanges 22 may be grasped and utilized as handles. Pad 10 may be left attached to garment 34 when the respirator is not in use, or the pad 10 may be removed and then reattached when the respirator is used again. Many patients only use respirators at night while sleeping, and then switch to a supplementary oxygen supply system during the day, so they may leave pad 10 attached to their stored sleeping garments during the day.

Although the invention has been described and illustrated in detail, such specific references are not meant to be overly limiting on the true scope of the invention as recited in the claims.

What I claim as my invention is:

1. A generally rectangular support pad structured for supporting a respirator hose in a generally straight-line approach to a patient's tracheostomy tube, and for dampening vibration in the respirator hose, and further for assisting in preventing fluid within the respirator hose from entering the patient's lungs through the tracheostomy tube while still allowing for a substantial degree of freedom of movement by the patient during use of said pad, said pad comprising;

an outer covering, said outer covering comprised of a single piece of flexible material folded in-two to define plural portions and a fold defining a first length side edge of said pad, a second lengthwise side edge of said pad being defined by a seam attaching two edges of said flexible material brought together by said fold, said second lengthwise side edge being oppositely disposed from said first lengthwise side edge, said pad further comprising a compressible and resilient inner material positioned centrally between the folded over portions of said flexible material defining said outer covering, said inner material maintained in position centrally in said pad by said fold and said seam defining said lengthwise side edges of said pad, said inner material further maintained in position by a first transverse seam and a second transverse seam, said first and said second transverse seams each spanning between said first and second lengthwise side edges of said pad so as to captively envelope said inner material between said lengthwise side edges of said pad and said first and said second transverse seams, said first transverse seam being placed adjacent and slightly inwardly from a first terminal end of said flexible material defining said outer covering of said pad, said second transverse seam being placed adjacent and slightly inwardly from a second terminal end of said flexible material defining said outer covering of said pad, said slightly inward positioning of the first and second transverse seams adjacent the respective terminal ends further defining a first flexible flange and an oppositely disposed second flexible flange each formed of said flexible material defining said outer covering of said pad, said flanges being suitably sized for use as handles, an elongated flexible belt affixable to a top exterior surface of said outer covering, said belt attachable at two oppositely disposed proximal ends of said belt to said outer covering by releasable attachment means, said belt being of a sufficient length so as to be able to be placed over the respirator hose when the respirator hose is resting on said top exterior surface of said outer covering simultaneously with both proximal ends of said belt being affixed to said outer covering, said belt further being of a sufficient length so as to allow the affixment of said belt over the respirator hose and to said outer covering with said belt being sufficiently loose so as to allow for a substantial degree of sliding movement of the respirator hose between said belt and said outer covering of said pad, a pad attachment means for releasably affixing said pad to a garment, said pad attachment means including mating hook and loop fastener sections attachable and detachable from one another, one section of the hook and loop fastener being affixed to an exterior bottom surface of said outer covering with the fastener portion thereof facing away from said outer covering, the mating hook and loop fastener section, to that affixed to said outer covering, having a pressure sensitive adhesive backing to provide for releasable attachment thereof to a garment with the hook and loop fastener portion thereof facing away from the garment to allow the mating hook and loop fastener sections to be releasibly attached together whereby said pad may be releasibly attached to a patient's garment.

2. A pad according to claim 1 wherein both proximal ends of said belt are releasibly affixed to said outer covering by means including hook and loop fasteners.

3. A pad according of claim 2 wherein said flexible material of said outer covering is a thin sheet material.

4. A pad according of claim 3 wherein said compressible and resilient inner material is a fiber batting material.

5. A method of using a support pad for supporting a respirator hose in a generally straight-line approach to a patient's tracheostomy tube when the patient is lying in bed, and for dampening vibration in the respirator hose, and further for assisting in preventing fluid within the respirator hose from entering the patient's lungs through the tracheostomy tube while still allowing for a substantial degree of freedom of movement by the patient during use of said pad and respirator hose, said pad being of a type having a compressible and resilient nature so as to be capable of dampening vibration in the respirator hose, said pad further including means to allow for releasibly attaching the pad to a garment worn by the patient, said pad further having an elongated flexible belt having two oppositely disposed proximal ends affixed to a top surface of the pad, at least one of the proximal ends of the belt affixed to the pad by releasable attachment means so as to allow the raising of the belt and the placing of the respirator hose thereunder, wherein said method comprises the steps of (a) attaching the pad to a garment of the patient in the central upper chest area, (b) lifting one of the proximal ends of the belt away from the pad, (c) placing a respirator hose, which is connected to a tracheostomy tube in the patient's throat, underneath the belt and on the top surface of the pad with the respirator hose extending toward the tracheostomy tube in a generally straight-line approach, (d) attaching the lifted proximal end of the belt to the top surface of the pad with the belt transversely over the respirator hose so as to leave the respirator hose captively restrained from falling off of the top surface of said pad, and further with the belt being sufficiently loosely placed and attached over said respirator hose so as to allow for a substantial degree of sliding movement of the respirator hose between the belt and the pad should the patient move his neck and tracheostomy tube relative to the support pad.

* * * * *